_United States Patent_ [19] [11] 4,117,108

Shapiro et al. [45] Sep. 26, 1978

[54] ORAL HYGIENE

[75] Inventors: Warren B. Shapiro, Randallstown; Owen Rodney Blackburne, Baltimore, both of Md.

[73] Assignee: Noxell Corporation, Baltimore, Md.

[21] Appl. No.: 721,746

[22] Filed: Sep. 9, 1976

Related U.S. Application Data

[63] Continuation-in-part of Ser. No. 623,277, Oct. 17, 1975.

[51] Int. Cl.² .......................... A61K 7/22; A61K 7/16
[52] U.S. Cl. ......................................... 424/54; 424/49
[58] Field of Search ....................................... 424/49–54, 424/248.51, 250, 267, 274

[56] References Cited

U.S. PATENT DOCUMENTS

| | | | |
|---|---|---|---|
| 2,187,823 | 1/1940 | Ulrich et al. | 260/404.5 R |
| 2,860,160 | 11/1958 | Sundberg et al. | 260/404.5 R |
| 2,888,383 | 5/1959 | Byrne | 424/54 |
| 3,998,945 | 12/1976 | Vit | 424/54 |

OTHER PUBLICATIONS

Noller, Chem. of Org. Cpds., 1965, Saunders Co., London, p. 209.
The Condensed Chem. Dictionary, 6th ed., Reinhold Publishing Corp., 1952, p. 290 (Coconut Acid).
L'Orange et al., "Composition... & Dental Protheses", Chem. Abst., vol. 84, 1976, paragraph 184919v.

_Primary Examiner_—Henry R. Jiles
_Assistant Examiner_—Cary Owens
_Attorney, Agent, or Firm_—Pollock, Vande Sande & Priddy

[57] ABSTRACT

Method for retarding pellicle and plaque formation which includes contacting sites of plaque formation and growth with dental preparation containing certain fatty acid amido compounds and/or salts thereof and dental preparations containing the fatty acid amido compounds and/or salts thereof.

46 Claims, No Drawings

ORAL HYGIENE

CROSS-REFERENCE TO RELATED CASES

This is a continuation-in-part application of copending U.S. Pat. application Ser. No. 623,277 filed Oct. 17, 1975 and entitled "Method and Composition for Improving Oral Hygiene".

BACKGROUND OF THE INVENTION

The present invention relates to a method for retarding pellicle and plaque formation and dental preparations employed for such purpose. More specifically, the present invention relates to a method for retarding pellicle and plaque formation by contacting sites of plaque formation and growth (e.g., the oral cavity) with certain fatty acid amido compounds and/or salts thereof and dental preparations containing the fatty acid amido compounds and/or salts thereof.

Dental pellicle is a soft deposit tenaciously held on the surfaces of the teeth which includes salivary protein. Dental plaque is a product of microbial growth is tenaciously attached to the surfaces of the teeth and adjacent gingiva, and exhibits a definite microscopic structure. If not removed, the plaque will become mineralized to form calculus and eventually lead to dental caries. Dental experts generally believe that calculus, also known as tartar, is dental plaque which has become mineralized with calcium phosphate, magnesium phosphate, calcium carbonate and other trace minerals found in the mouth. If calculus is not removed from around the teeth and under the gum, inflammation can result which can ultimately lead to periodontal disease and subsequent tooth loss.

Although plaque can be removed from the teeth by thorough abrasive action, it quickly reforms on the tooth surface. Accordingly, the incidence of dental calculus and subsequent periodontal disease can be reduced by reducing or preventing the deposition of plaque and by means which prevent mineralization of the plaque.

It is therefore an object of the present invention to provide a method for retarding pellicle and plaque formation, and to provide compositions containing active ingredients which retard pellicle and plaque deposition. Another object of the present invention is to provide nontoxic dentifrice preparations for retarding pellicle and plaque formation. The dentifrice preparations include toothpastes, dental creams, tooth powders, mouthwashes, lozenges, tablets, aerosol sprays, chewing gum, toothpicks, dental floss, denture cleansers, and the like.

SUMMARY OF THE INVENTION

One aspect of the present invention is a method for retarding pellicle and plaque deposition which comprises intermittently contacting sites of plaque formation and growth with a preparation comprising, in an amount sufficient to retard pellicle and plaque formation, a compound of the formula:

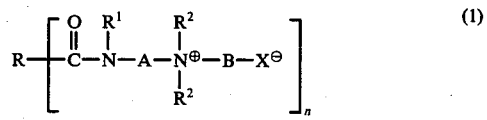

wherein R is a monovalent or divalent hydrocarbyl group containing at least 14 carbon atoms, $n$ is one when R is monovalent and is 2 when R is divalent; $R_1$ is H or an alkyl group containing from 1 to about 3 carbon atoms; A is a divalent hydrocarbon bridge containing from 1 to about 6 carbon atoms; B is a divalent alkylene or alkylidene bridge containing from 1 or 2 carbon atoms; each $R_2$ individually is an alkyl group containing from 1 to about 5 carbon atoms; or both $R_2$ groups are interconnected to form a heterocyclic ring with the N atom to which they are attached and containing 5 to 6 members in the ring; and X is a carboxylate or sulfonate group; and/or nontoxic, physiologically and orally acceptable salts of said compound.

The present invention is also concerned with certain dentifrice preparations containing an amount sufficient to retard pellicle and plaque formation of a compound of formula (1) above and/or nontoxic, physiologically and orally acceptable salts of said compound of formula (1).

DESCRIPTION OF PREFERRED EMBODIMENTS

The objectives of the present invention are accomplished by dental preparations which contain a compound of the formula:

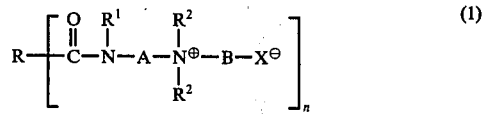

wherein R in the above formula is a hydrocarbyl group containing at least 14 carbon atoms. R usually contains no more than about 21 carbon atoms, and preferably from 15 to about 21 carbon atoms; and most preferably from 15 to about 17 carbon atoms. Examples of some suitable hydrocarbyl groups include aliphatic hydrocarbon groups; alkaryl groups; aralkyl; alkacycloalkyl groups; and cycloalkalkyl groups. The preferred hydrocarbyl group is aliphatic hydrocarbon group. The aliphatic hydrocarbon group can be saturated or can be ethylenically unsaturated and can be straight chain or branched chain. Examples of some suitable aliphatic hydrocarbon groups include pentadecyl, heptadecyl, tetradecyl, and heptadecenyl. The aryl portion of the alkaryl and aralkyl groups include phenyl and naphthyl. The cycloalkyl portion of the alkacycloalkyl and cycloalkyl groups include cyclopropyl, cyclobutyl and cyclohexyl. R can be monovalent or divalent and is preferably monovalent. When R is monovalent, $n$ is 1 and when R is divalent, $n$ is 2.

$R_1$ is hydrogen or an alkyl group containing from 1 to about 3 carbon atoms such as methyl, ethyl, and propyl. $R_1$ is preferably hydrogen or methyl and most preferably is hydrogen.

A is a divalent hydrocarbon bridge containing from 1 to about 6 carbon atoms. A can be straight chain or branched chain and includes alkylene groups, alkylidene groups, cycloalkylene groups, and arylene groups. Examples of some suitable alkylene groups include methylene, ethylene, propylene, butylene, pentylene and hexylene. Examples of some suitable alkylidene groups include ethylidene and isopropylidene. Examples of cycloalkylene groups include cyclopropylene, cyclobutylene, cyclopentylene, and cyclohexylene. An example of an arylene group includes phenylene. Preferably A is an alkylene or alkylidene group. Most preferably A is an alkylene or alkylidene group containing 1 to 3 carbon atoms.

B is a divalent alkylene or alkylidene bridge containing 1 or 2 carbon atoms. Examples of some suitable alkylene groups include methylene and ethylene. An example of a suitable alkylidene group includes ethylidene.

X is a carboxylate [COO] or a sulfonate

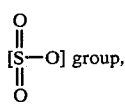

group, and preferably is a carboxylate group. It has been observed that compounds wherein X is carboxylate provided greater inhibition against pellicle and plaque formation as compared to compounds wherein X is sulfonate. Moreover, compounds wherein X is carboxylate are preferred since such compounds can be used with water as the carrier; whereas, those compounds wherein X is sulfonate are not readily dispersible in water and require an organic carrier such as propylene glycol.

Each $R_2$ individually is an alkyl group containing from 1 to about 5 carbon atoms; or both $R_2$ groups are interconnected to form a heterocyclic ring with the N atom to which they are attached and containing 5 to 6 members in the ring. Examples of some heterocyclic rings include morpholinyl, piperidinyl, pyrrolidinyl, and piperazinyl. Preferably $R_2$ is an alkyl group. The alkyl group preferably contains 1 to 3 carbon atoms and most preferably is methyl.

The preferred compounds employed in the present invention have the following structural formula:

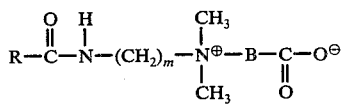

wherein R is an aliphatic hydrocarbon group containing at least 14 carbon atoms; B is the same as defined hereinabove, and m is a whole number integer from 1 to 3; and/or nontoxic, physiologically and orally acceptable salts of the compound of formula (2).

Examples of some specific compounds suitable for the present invention include compounds of the following structural formula:

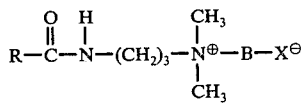

wherein

| R | B | X | Name |
|---|---|---|---|
| pentadecyl | $CH_2$ | $\overset{O}{\underset{\|}{C}}\!-\!O$ | palmitic amido betaine |
| heptadecyl | $CH_2$ | $\overset{O}{\underset{\|}{C}}\!-\!O$ | stearic amido betaine |
| heptadecenyl | $CH_2$ | $\overset{O}{\underset{\|}{C}}\!-\!O$ | oleic amido betaine |

-continued

| R | B | X | Name |
|---|---|---|---|
| pentadecyl | —CH—<br>  \|<br>  $CH_3$ | C—O<br>\|\|<br>O | DL-N-carboxymethyl-methyl-N,N-dimethyl-N-(3-palmitamido-propyl)-ammonium betaine |
| pentadecyl | $(CH_2)_2$ | C—O<br>\|\|<br>O | N-carboxyethyl-N,N-dimethyl-N-(3-palmitamido-propyl)-ammonium betaine |
| heptadecenyl | —CH—<br>  \|<br>  $CH_3$ | C—O<br>\|\|<br>O | DL-N-carboxymethylmethyl-N,N-dimethyl-N-(3-oleyl-amidopropyl)-ammonium-betaine |
| heptadecenyl | $(CH_2)_2$ | C—O<br>\|\|<br>O | N-carboxyethyl-N,N-dimethyl-N-(3-oleyl-amidopropyl)-ammonium betaine |
| heptadecyl | —CH—<br>  \|<br>  $CH_3$ | C—O<br>\|\|<br>O | DL-N-carboxymethylmethyl-N,N-dimethyl-N-(3-stear-amidopropyl)-ammonium betaine |
| heptadecyl | —$(CH_2)_2$ | C—O<br>\|\|<br>O | N-carboxyethyl-N,N-dimethyl-N-(3-stearamido-propyl)-ammonium betaine |
| pentadecyl | $(CH_2)_2$ | O<br>\|\|<br>S—O<br>\|\|<br>O | 2-[N,N-dimethyl-N-(3-palmitamidopropyl)-amino] ethanesulfobetaine |
| heptadecenyl | $(CH_2)_2$ | O<br>\|\|<br>S—O<br>\|\|<br>O | 2-[N,N-dimethyl-N-(3-oleylamidopropyl)-amino] ethanesulfobetaine |
| heptadecyl | $(CH_2)_2$ | O<br>\|\|<br>S—O<br>\|\|<br>O | 2-[N,N-dimethyl-N-(3-stearamidopropyl)-amino] ethanesulfobetaine |

In addition, nontoxic salts suitable for use in human oral cavity include both acid and base addition salts of the above compounds can be used in the present invention. Suitable salts include citrate, acetate, maleate, lactate, and phosphate salts.

It has been observed that compounds similar to those employed according to the present invention, except that R contains less than 14 carbon atoms, do not retard plaque and pellicle deposition as achieved by the present invention. In particular, it has been observed that coconut amido betaine available under the trade designation Tegobetaine C from T. H. Goldschmidt, and lauric myristic amido betaine available under the trade designation Schercotaine LMAB from Scher Brothers, Inc., Clifton, N.J. do not provide plaque inhibition activity. Tegobetaine C is a coconut amido propyl betaine having the general structure described above in formula (3) except that

is from a coconut fatty acid which presumably includes minor amounts of fatty acids having 15 carbon atoms or more. However, in view of the small quantities of R groups having at least 14 carbon atoms in Tegobetaine C, the concentration of compounds of the type falling within the scope of this invention, are apparently not sufficient to retard the formation of plaque and pellicle.

In addition, as will be shown hereinbelow, Denta Fresh ® a denture cleanser commercially available from Noxell, the assignee of the present application, which contains about 15% by weight of Tegobetaine C does not inhibit the formation of plaque. With respect to Denta Fresh ®, it is believed that not only is the amount of compounds within the scope of the present invention insufficient to retard plaque and pellicle formation but also that the formulation includes materials such as sodium lauryl sulfate which may interact with the betaines in the composition to provide products of a type that do not exhibit plaque retarding properties. This is demonstrated by the fact that betaines within the scope of the present invention were used in place of Tegobetaine C in Denta Fresh ® but such compositions still did not retard plaque formation as will be shown hereinbelow. In particular, see Examples 17A-C.

Various of the compounds suitable for the present invention are available. For instance, a preparation containing isostearic amido betaine is available under the trade designation Schercotaine IAB, and a preparation containing palmitic amido betaine is available under the trade designation Schercotaine PAB from Scher Brothers, Inc. A discussion of various amido compounds including those suitable for use in the present invention as well as those outside the scope of the present invention can be found in a publication entitled "Tegobetaine Chemistry," Goldschmidt Chemical Corporation, 153 Waverly Place, New York City, N.Y., and in U.S. Pat. No. 3,280,179 to Ernst, disclosures of which are incorporated herein by reference.

The compounds suitable for the present invention can be prepared, for instance, by reacting a diamine of the formula:

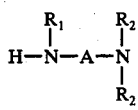

(4)

with a mono- or dicarboxylic acid of the formula:

(5)

to provide an amido amine of the formula:

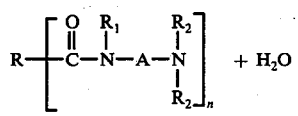 + H$_2$O (6)

The progress of this reaction can be readily monitored by measuring the amount of water formed. When a monocarboxylic acid is employed, the acid and amine are used in about equimolar quantities. When a dicarboxylic acid is employed, the molar ratio of acid to amine is about 1:2. After the amidoamine is isolated from the reaction mixture, it is reacted with a quaternizing agent such as chloroacetic acid, 2-chloropropionic acid, 3-chloropropionic acid, and sodium salt of 2-chloroethane-sulfonic acid, according to the following reaction which shows chloroacetic acid as an exemplary reactant for convenience to provide compounds employed according to the present invention.

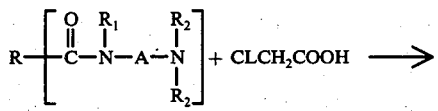 + ClCH$_2$COOH ⟶

-continued

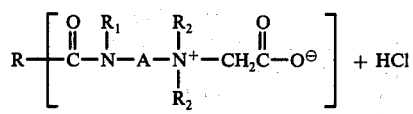 + HCl

This latter reaction can be carried out under reflux for convenience when desired. The meanings of R, R$_1$, R$_2$, n, and A are the same as discussed hereinabove.

Examples of some diamines of formula (4) include 3-dimethylaminopropylamine; para-aminodiethylaniline; para-aminodimethylaniline; N-aminoethylpiperazine; N-aminopropylmorpholine; 3-diethylaminopropylamine; 3-ethylmethylaminopropylamine; and dimethylaminomethylamine.

Examples of some carboxylic acids of formula (5) include stearic acid; behenic acid; isostearic acid; palmitic acid; oleic acid; linoleic acid; linolenic acid; erucic acid; and pentadecanoic acid.

The fatty acid amido compounds employed according to the present invention are intermittently contacted with sites of plaque formation and growth such as the oral cavity in the form of a dental preparation. The fatty acid amido compounds can be utilized to retard pellicle and plaque formation on dentures by soaking dentures in a suitable preparation. Accordingly, sites of plaque formation and growth as used herein refer to the oral cavity as well as dentures or false teeth while located in or out of the oral cavity.

The term "dental preparation" which is used herein is intended to designate products which in the ordinary course of usage are retained in contact with sites for plaque formation and growth such as in the human oral cavity for a time sufficient to contact substantially all of the dental surfaces but are not intentionally ingested.

When the fatty acid amido compounds are to be utilized in the oral cavity, such compounds are provided in a nontoxic carrier suitable for use in the oral cavity. For example, the fatty acid amido compounds when X is carboxylate can be dispersed in water and used as such. Some preparations to which the present invention are directed include toothpastes, dental creams, tooth powders, mouth rinses, lozenges, tablets, aerosol sprays, chewing gum, dental floss, toothpicks, and denture cleansers. The amount of the fatty acid amido compound employed according to the present invention is at least sufficient to provide a composition which retards pellicle and plaque formation and is generally at least about 1% by weight and preferably at least about 5% by weight of the fatty acid amido compound in the dental preparation. The maximum amount of fatty acid amido compound is dependent primarily upon economical and practical considerations and is generally about 25% by weight in the dental preparation.

In addition, the threshold effective amount of any fatty acid amido compound is not only dependent upon the absolute quantity of the fatty acid amido compound in the preparation but may also be dependent somewhat upon the amount of the fatty acid amido compound relative to other constituents in the particular preparation, and the type of other constituents in the particular preparation. For instance, if the preparation contains an ingredient which interacts with the fatty acid amido compound to render it inactive, it is apparent that the amount of amido compound must be in excess of that which is interacted. Furthermore, the degree of rinsing after a treatment may have some effect upon the amount necessary. For instance, little or no rinsing may result in some buildup of the compound on the teeth which would reduce the amount needed in subsequent treatments. The minimum amount of the fatty acid amido compound required for any particular preparation is readily ascertainable without undue experimentation.

That the minimum effective amount is not dependent solely upon the absolute quantity of the fatty acid amido compound is emphasized by the observation that compositions containing about 2.5% palmitic amido betaine or less, about 10% ethyl alcohol, up to about 5% NaCl and the remainder being water; and compositions containing about 2.5% palmitic amido betaine, about 10% by weight of silica, about 56% by weight sorbitol, up to 5% NaCl and the remainder water, did not retard plaque formation; whereas, compositions the same as the above compositions except that no rinsing was carried out after treatment therewith, prevented the formation of plaque. In addition, it has been observed that compositions containing about 5% palmitic amido betaine and about 95% water retarded plaque formation; whereas, compositions containing about 5% palmitic amido betaine, about 8% of silica, about 50.5% of sorbitol, and about 36.5% by weight of water were marginally effective in that sometimes the composition exhibited retardation of plaque while other times the composition did not.

It was further observed that various compositions containing about 5% isostearic amido betaine or 5% stearic amido betaine including one which contained about 5% by weight of isostearic amido betaine, about 24% by weight of glycerin, about 1% by weight of propylene glycol, about 0.75% by weight of carboxymethyl cellulose, and about 69.25% by weight of water did not exhibit plaque inhibition activity; whereas, a composition containing about 5% by weight of isostearic amido betaine and being similar to the above composition except that it contained about 0.75% of hydroxyethyl cellulose in place of the carboxymethyl cellulose retarded plaque formation and exhibited moderate plaque inhibition.

When preparing dental preparations according to the present invention and particularly for application in the oral cavity, carriers and other additives suitable for the oral cavity and which are compatible with the fatty acid amido compound and each other such as, for example, sudsing agents, flavoring agents, abrasive polishing compounds, humectants, and sweetening agents can be employed. The amount and type of these additive materials used can be varied greatly. In addition, the pH of dental preparations employed according to the present invention and particularly those for use in the oral cavity is usually between about 3 and about 9, and preferably between about 5 and about 7.5. The additives and pH for denture preparations not to be used in the oral cavity need not be suitable for the oral cavity.

Examples of some suitable water-insoluble abrasive polishing agents include dicalcium phosphate, hydrated aluminum oxide, calcium carbonate, calcium polymetaphosphate, dicalcium orthophosphate dihydrate, sodium polymetaphosphate, and various resinous abrasive materials such as particulate polyethylene, melamines, phenolics, ureas, melamine-ureas, melamine-formaldehydes, urea-formaldehydes, melamine-urea-formaldehydes, and cross-linked polyesters. Mixtures of abrasive polishing agents can be employed when desired.

A preferred abrasive agent is hydrated aluminum oxide since it has been observed that preparations of the present invention containing hydrated aluminum oxide exhibit greater plaque inhibition as compared to preparations containing certain phosphate abrasives. Although not preferred, the phosphate abrasives can be employed when desired since the fatty acid amido compounds demonstrate plaque inhibition in their presence, the degree of which is dependent somewhat upon their respective concentrations. The total amount of abrasive agent, when present, can range from about 0.5% to about 95% by weight of the dental preparation. Preferably toothpastes contain from about 5 to about 60% by weight of abrasive with the abrasive particle size preferably ranging from about 2 microns to about 20 microns.

Suitable sudsing agents for use according to the present invention are those which are reasonably stable and form suds throughout a wide pH range and are acceptable for use in the oral cavity. Examples of some suitable sudsing agents include water-soluble salts of sulfonated monoglycerides of fatty acids having from about 10 to about 18 carbon atoms such as sodium coconut monoglyceride sulfonate; water-soluble salts of fatty acid amines of taurine such as sodium N-methyl-N-palmitoyl tauride; water-soluble salts of fatty acid esters of isethionic acid such as the coconut acid ester of sodium isethionate; substantially saturated aliphatic acyl amides of saturated aliphatic monoamino carboxylic acid having from about 2 to about 6 carbon atoms and in which the acyl radical contains from about 12 to about 16 carbon atoms such as sodium N-lauroyl sarcosinate; and the polyoxyalkylene polyols such as the Pluronics from Wyandotte Corporation. Likewise, mixtures of the sudsing agents can be employed when desired. Generally, the sudsing agent, when present, is employed in amounts ranging from about 0.5% to about 5.0% by weight.

Moreover, when desired, flavoring agents can be included in the dental preparations employed according to the present invention and include such flavoring agents as oil of wintergreen, oil of peppermint, oil of anise, citrus flavors, and vanillin. Likewise, various sweetening agents such as, for example, saccharin, dextrose, mannitol, levulose, and sodium cyclamate can be employed when desired.

In certain of the compositions contemplated by the present invention, such as toothpaste, it is generally desirable to employ thickening agents, exemplary of which are hydroxyethyl cellulose, water-soluble salts of cellulose ethers, including sodium carboxymethyl cellulose and sodium carboxymethylhydroxyethyl cellulose, and natural gums such as gum karaya, gum arabic and gum tragacanth. In addition, colloidal magnesium aluminum silicate or finely divided silica much as silica aerogels and microfine precipitated silicas can be used as part of the thickening agent to further improve texture in such compositions as toothpastes. The thickening agents are generally employed in amounts from about 0.1 to about 15% by weight when utilized.

The preferred thickening agents are the natural gums and finely divided silica, particularly since it has been observed that preparations of the present invention containing such thickening agents exhibit greater plaque inhibition as compared to preparations containing certain other thickening agents in certain amounts such as hydroxyethyl cellulose, sodium carboxymethyl cellulose, and magnesium aluminum silicate. Although not preferred, the above thickening agents can be used when desired since the fatty acid amido compounds demonstrate plaque inhibition in their presence, the degree of which is dependent somewhat upon their respective concentrations.

In addition, in certain of the dental preparations employed in the present invention, such as toothpastes, it may be desirable to include a humectant or a viscosity modifying material. Examples of some suitable humectants include nontoxic polyhydric alcohols such as glycerin, sorbitol, mannitol, propylene glycol, polyethylene glycol, polypropylene glycol, and mixtures thereof. The humectants are generally present in amounts up to about 40% by weight of the dental preparation.

A typical toothpaste of the present invention can contain the amido compound in an amount sufficient to retard plaque and pellicle formation, from about 5% to about 60% by weight of an abrasive polishing agent, from about 0.5% to about 5% by weight of a sudsing agent, from about 0.1% to about 15% by weight of a thickening agent, and the balance being substantially water and humectants. A typical mouthwash composition suitable for practicing the present invention can contain the amido compound in an amount sufficient to retard pellicle and plaque formation, a sudsing agent, ethyl alcohol, hemectant, sweetener, flavor, and water. A typical chewing gum composition useful for the present invention can contain the amido compound in an amount sufficient to retard pellicle and plaque formation, and a gum base. A prophylactic paste suitable for the present invention can include the amido compound in an amount sufficient to retard pellicle and plaque formation and pumice.

In addition, the present invention can be practiced by coating and impregnating dental floss or toothpicks with a composition containing the amido compound of the present invention. The coating operation can be carried out by any means well known for coating and impregnating fibers such as by passing dental floss or toothpicks through an aqueous bath of the amido compounds and then permitting the water to evaporate, e.g., by heating under vacuum.

The following nonlimiting examples are provided to further demonstrate the present invention.

EXAMPLE 1 - PART A

A set of three extracted human teeth without the roots is mounted on a plastic strip of about 1 inch × 3 inches. The teeth are then swabbed with human saliva using a sterile Dacron swab and allowed to dry for about 15 minutes. The strip is then placed in a petri dish and covered with about 200 ml of an aqueous solution of about 2% trypticase and about 4% sucrose. Each dish is then inoculated with an additional 1 ml of human saliva and then incubated at about 37° C for about 24 hours.

Next, the set of teeth is removed from the media, dried, and then dipped into a 0.5% aqueous solution of FD & C RED No. 3 to visually disclose the plaque. The strip is then rinsed under tap water.

The teeth show heavy plaque growth. The teeth are then brushed with an electric toothbrush fitted with a soft nylon brush carrying a composition containing about 25% by weight of a palmitic amido betaine, about 2–5% NaCl and the remainder water, available under the trade designation Scherocotaine PAB, until all of the red disclosed plaque is removed and are then rinsed.

The teeth are then again swabbed with human saliva, placed in a petri dish covered with the trypticase-sucrose media, which is then inoculated with an additional 1 ml of saliva and incubated for about 24 hours at about 37° C. At the end of the 24 hours, the set of teeth is removed from the media, dried, and dipped into a 0.5% FD & C RED No. 3 solution for about 60 seconds to visually disclose the presence of plaque and is then rinsed under tap water. No plaque growth is observed on the teeth brushed with the Schercotaine PAB. The palmitic amido betaine effectively inhibits the redeposition of dental plaque on the teeth.

Comparison — Part B

The general procedure of Part A of this example is repeated except that the set of teeth employed is brushed with water until all of the red disclosed plaque is removed. The results after the second 24-hour incubation show heavy plaque growth on the teeth brushed with water.

Comparison — Part C

The general procedure of Part A of this example is repeated except that the set of teeth employed is brushed with a stannous fluoride toothpaste commercially available under the trade designation "Crest" until all of the red disclosed plaque is removed. The results after the second 24-hour incubation period show heavy plaque growth on the teeth brushed with said toothpaste.

A comparison between Part A of this example and Parts B and C illustrates the effectiveness of the amido alkyl betaines employed according to the present invention for inhibiting plaque formation.

EXAMPLE 2

The general procedure of Example 1A is repeated except that the set of teeth employed is brushed with a composition of about 20% by weight of palmitic amido betaine, about 10% by weight ethyl alcohol, and about 70% by weight of water. The results after the second 24-hour incubation period indicate that the preparation provides pellicle and plaque inhibition although not as great as the preparation employed in Example 1A.

EXAMPLE 3

The general procedure of Example 1A is repeated except that the set of teeth employed is brushed with a composition containing about 35% by weight of isostearic amido betaine, about 2–5% NaCl and the remainder water, available under the trade designation Schercotaine IAB. The results after the second 24-hour incubation period show that the isostearic amido betaine provides good plaque and pellicle inhibition.

EXAMPLE 4

The general procedure of Example 1A is repeated except that the set of teeth employed is brushed with a composition containing about 10% by weight of the palmitic amido betaine, about 8% by weight of silica gel having an average particle size of 4 $\mu$ and surface area of 310 $m^2$/gm and available under the trade designation Syloid 244 from Davison Chemical; about 36.4% by weight of sorbitol, up to about 5% by weight of NaCl, and the remainder water. The composition is prepared by adding the silica gel to the sorbitol and a portion of the water with mixing until a homogeneous solution is obtained. After this, an aqueous dispersion of the palmitic amido betaine (Schercotaine PAB) is added and admixed until a uniform composition is obtained. The results after the second 24-hour incubation show complete prevention of pellicle and plaque formation on the teeth.

EXAMPLE 5

The general procedure of Example 1A is repeated except that the set of teeth employed is brushed with and dipped into a composition containing about 2.5% by weight palmitic amido betaine, about 10% by weight of ethyl alcohol, up to about 5% NaCl and the remainder water. Also, the teeth are not rinsed after the brushing. After the second incubation period of 24 hours, there is no pellicle or plaque formation on the set of teeth.

EXAMPLE 6

The general procedure of Example 1A is repeated except that the set of teeth employed is brushed with a composition containing about 5% by weight of isostearic amido betaine, about 24% by weight of glycerin, about 0.75% by weight of hydroxyethyl cellulose, about 1% by weight of propylene glycol, up to about 5% by weight of NaCl, and the remainder water. The composition is prepared by heating the glycerin to about 70° C, and then adding the hydroxyethyl cellulose with stirring. Next a portion of the water is added while heating and stirring for about 15 minutes. The composition is thn cooled and a composition of propylene glycol, and a mixture of the betaine, NaCl, and the rest of the water (the mixture being available under the trade designation Schercotaine IAB) is added. The results after the second 24-hour incubation period show that the composition exhibits moderate pellicle and plaque inhibition.

EXAMPLE 7

Example 1A is repeated except that the set of teeth employed is brushed with a composition containing about 25% by weight of oleic amido betaine, up to about 5% by weight of NaCl and the remainder water (available under the trade designation Schercotaine OAB). The results of the tests after the second 24-hour incubation period indicate that the composition provides almost complete inhibition of pellicle and plaque growth on the teeth.

EXAMPLE 8

The general procedure of Example 1A is repeated except that the set of teeth employed is brushed with the composition containing about 10 parts by weight of palmitic amido betaine, about 35.7 parts by weight of sorbitol, about 8 parts by weight of a silica available as QUSO G-30 from Philadelphia Quartz Co., about 1 part by weight of propylene glycol, up to about 2 parts by weight of NaCl, and about 45 parts by weight of water are employed. The composition is prepared by adding the silica to the sorbitol and a portion of the water and mixing until a uniform transparent gel is obtained. Next the propylene glycol is mixed with a combination of the remainder of the water, betaine, and NaCl (available under the trade designation Schercotaine PAB). Then this mixture of the propylene glycol, betaine, water, and NaCl is added to the silica, sorbitol, and a water mixture and agitated until a uniform mixture is obtained. The results of the tests after the second 24-hour incubation period indicate that the composition provides complete pellicle and plaque inhibition on the teeth.

EXAMPLE 9

The general procedure of Example 1A is repeated except that the set of teeth employed is brushed with a composition containing about 10 parts by weight of palmitic amido betaine, about 35.7 parts by weight of sorbitol, about 8 parts by weight of a silica available at QUSO G-32 from Philadelphia Quartz Company, about 1 part by weight of propylene glycol, up to about 1.5 parts by weight of NaCl, and about 45 parts by weight of water. The composition is prepared along the general procedure for preparation of the composition in Example 8. The test results after the second 24-hour incubation period indicate that the composition provides complete inhibition of pellicle and plaque growth.

EXAMPLE 10

The general procedure of Example 1A is repeated except that the set of teeth is brushed with a solution of about 10% by weight of a purified palmitic amido betaine and about 90% by weight of water. The purified palmitic amido betaine is obtained by placing about 200 parts by weight of Schercotaine PAB in an evaporating dish, and placing the dish in a vacuum of about 26 inches of Hg and heating to about 65° C. The composition is maintained for about 48 hours in the oven. After this, the composition is heated in a vacuum of about 28 inches of Hg, at about 65° C for about another 8 hours. Next, the residue is placed in a 400 ml beaker and 300 ml of 95% ethyl alcohol are added and the mixture stirred until a solution of the betaine is obtained. The mixture is then filtered and a precipitate of sodium chloride is discarded. The filtrate is then concentrated to about 100 mls on a steam bath, cooled and then 200 mls of acetone are added. A white precipitate is formed. The precipitate is filtered and rinsed on a Buchner funnel. The precipitate is transferred to an evaporating dish and left overnight at 65° C under 28 inches of vacuum. The precipitate becomes a yellow amorphous solid. The solid is then precipitated from the ethyl alcohol-acetone mixture and the resulting precipitate allowed to dry in air until all the acetone vapors are evaporated. A white solid material remains. This material is then dissolved in water to provide the above-mentioned composition. The results of the tests after the 24-hour incubation period indicate that the composition provides complete inhibition of plaque and pellicle growth on the teeth.

EXAMPLE 11

The general procedure of Example 1A is repeated except that the set of teeth employed is brushed with a composition containing about 5% by weight of a purified palmitic amido betaine obtained along the lines of Example 10, and about 95% by weight of water. The results of the tests after the 24-hour incubation period indicate that the composition provides partial inhibition of plaque and pellicle growth on the teeth.

EXAMPLE 12

The general procedure of Example 1A is repeated except that the set of teeth employed is brushed with a composition obtained by the following procedure. About 80 parts by weight of sorbitol, about 34 parts by weight of water, and about 10.2 parts by weight of glycerin are heated to about 65° C. Next about 0.3 parts by weight of sodium benzoate are added to the mixture. About 1.5 parts by weight of carboxymethyl cellulose are added to the above composition while continuously stirring until a uniform mixture is obtained. To this composition is added a mixture of about 24 parts by weight of a silica gel available under the trade designation Syloid 244 from Davision Chemical, and about 30 parts by weight of hydrated alumina having an average particle size of about 12.5 μ and available under the trade designation Kleen-Dent TA-6 from Reheis Chemical with stirring at about room temperature. About 30 parts by weight of palmitic amido betaine, up to about 5 parts by weight of NaCl, and about 90 parts by weight of water are added to the mixture. The pH of the composition is about 6.4. The palmitic amido betaine portion is from Schercotaine PAB. The results of the tests after the second 24-hour incubation period indicate that the composition provides complete inhibition of pellicle and plaque growth on the teeth.

EXAMPLE 13

The general procedure of Example 1A is repeated except that the set of teeth employed is brushed with a composition prepared according to the following procedure. About 66.5 parts by weight of sorbitol and about 73.5 parts by weight of water are heated to about 60° C. About 0.25 parts by weight of sodium benzoate are added with mixing, followed by the addition of about 1.25 parts by weight of carboxymethyl cellulose gradually while mixing until a uniform gel is obtained. The composition is then cooled to room temperature and deaerated. About 25 parts by weight of a hydrated alumina available under the trade designation Kleen Dent TA-6 from Reheis Chemical Company are added with agitation. The composition is then mixed with about 28 parts by weight of a silica gel available under the trade designation Syloid 244 from Davison Chemical with agitation until a uniform composition is obtained. The composition is then again deaerated. A mixture of about 25 parts by weight of palmitic amido betaine as purified according to Example 10, about 8.5 parts by weight of glycerin, and about 25 parts by weight of water are added to the composition and the materials are mixed until a homogeneous deaerated paste is obtained. The results of the tests after the second 24-hour incubation period indicate that the composition provides complete plaque and pellicle inhibition on the teeth.

EXAMPLE 14

The general procedure of Example 1A is repeated except that the set of teeth employed is brushed with a composition prepared according to the following procedure. About 6 parts by weight of a polyoxypropyleneoxyethylene available under the trade designation Pluronic F-68 from Wyandotte Corporation are dissolved in about 60 parts by weight of water. About 0.3 parts of sodium benzoate are added to about 108 parts of a mixture of about 75.5 parts by weight of sorbitol and about 22.5 parts by weight of water, which in turn are added to the aqueous Pluronic composition. About 0.5 parts of carboxymethyl cellulose are then added with vigorous agitation until a uniform composition is obtained. The composition is then deaerated. About 30 parts by weight of a hydrated alumina available under the trade designation Kleen Dent TA6 from Reheis Chemical are added and admixed with agitation until a uniform composition is obtained. This is followed by the addition of about 24 parts by weight of a silica gel available from Davison Chemical under the trade designation Syloid 244 with mixing and agitation until a uniform composition is obtained. After this, a composition containing about 30 parts by weight of a purified palmitic amido betaine as prepared according to Example 10, about 10.2 parts by weight of glycerin, and about 21 parts by weight of distilled water are added to the above composition and mixing is continued until a homogeneous composition is obtained. The results of the tests after the second 24-hour incubation period indicate that the composition provides complete inhibition of plaque and pellicle growth on the teeth.

EXAMPLE 15

The general procedure of Example 1A is repeated except that the set of teeth employed is brushed with a composition of about 14% by weight isostearic amido betaine and about 86% by weight of water. After the second 24-hour incubation period, no plaque and pellicle are present on the teeth.

COMPARISON EXAMPLE 16

The general procedure of Example 1A is repeated except that in place of the set of teeth employed, polymethyl methacrylate strips (which are sanded perpendicular to their lengths to remove the polished surface) are brushed with a composition of Tegobetaine C (a coconut fatty acid amido betaine). The results of the tests after the 24-hour incubation period show that the Tegobetaine C does not prevent the growth of plaque and/or pellicle.

EXAMPLE 17A

The general procedure of Example 16 is repeated except that the polymethylacrylate strips are brushed with Denta Fresh ®, a commercial denture cleanser available from Noxell, the assignee of the present application, which contains about 15% by weight of Tegobetaine C. The results of the tests after the second 24-hour incubation period indicate that the Denta Fresh ® does not provide any inhibition of plaque and/or pellicle growth.

EXAMPLE 17B

The general procedure of Part A of Example 17 is repeated except that the polymethylmethacrylate strips are brushed with a composition containing the same ingredients as Denta Fresh ® except that the Tegobetaine C is replaced with 15% by weight of palmitic amido betaine. The results of the tests after the second 24-hour incubation period indicate that the composition does not prevent plaque and/or pellicle growth.

EXAMPLE 17C

The general procedure of Part A of Example 17 is repeated except that the polymethylmethacrylate strips are brushed with a composition containing the same ingredients as Denta Fresh ® except that the Tegobetaine C is replaced with 15% by weight of isostearic amido betaine. The results of the tests after the second 24-hour incubation period indicate that the composition does not prevent plaque and/or pellicle growth.

The results of Example 17, Parts A-C, indicate that the Denta Fresh ® contains a material, apparently sodium lauryl sulfate, which interacts with the betaine to render it ineffective for the purposes of the present invention.

EXAMPLE 18

The general procedure of Example 16 is repeated except that the methylmethacrylate strips are brushed with Schercotaine LMAB (an aqueous preparation of lauric myristic amido betaine). The results of the tests after the second 24-hour incubation period indicate that the lauric myristic amido betaine does not prevent plaque and/or pellicle formation.

All of the above examples employed new sets of teeth or plastic strips and new brushes for the brushing, respectively. Any NaCl present in the composition is due to its presence in the available compositions of the fatty acid amido compounds.

EXAMPLE 19

An acute oral $LD_{50}$ study was done on rats for Schercotaine PAB in mature albino rats. The post-dose observations were characterized by diarrhea and general weakness within the first 48 hours. The resulting mortality pattern was wide ranging and the $LD_{50}$ was calculated to be 6000 mg/kg of body weight with 95% confidence limits of 8040 to 4477 mg/kg for the material tested.

Palmitic amido betaine purified according to Example 10 is also tested according to the above procedure.

The $LD_{50}$ was calculated to be 2400 mg/kg (2832–2033 mg/kg) at 95% confidence limit.

EXAMPLE 20

A set of three extracted human teeth without the roots is mounted on a polymethylmethacrylate plastic strip of about 1 inch × 3 inches. A drop of human saliva is applied to each tooth and allowed to dry. The set of teeth is then placed in a petri dish and covered with about 200 ml of an aqueous solution of about 2% trypticase and about 4% sucrose. The dish is then inoculated with an additional 1 ml of human saliva and then incubated at about 37° C for about 24 hours.

Next, the set of teeth is removed from the media, rinsed, and then dipped into a 0.5% aqueous solution of FD & C RED No. 3 to visually disclose the plaque.

The teeth show heavy plaque growth. The teeth are then brushed with water using an electric toothbrush fitted with a soft nylon brush until all of the red disclosed plaque and/or pellicle is removed.

The teeth are then swabbed with human saliva, placed in a petri dish covered with about 200 ml of the trypticase-sucrose media and about 0.1 ml of a composition containing 1% by weight DL-N-carboxymethylmethyl-N,N-dimethyl-N-(3-palmitamidopropyl) ammonium betaine and the remainder being distilled water. The contents of the dish are then inoculated with an additional 1 ml of saliva and incubated for about 24 hours at about 37° C. At the end of the 24 hours, the set of teeth is removed from the media, dried, and dipped into a 0.5% FE & C RED No. 3 solution for about 60 seconds to visually disclose the presence of pellicle and plaque and is then rinsed under tap water. No pellicle and plaque growth are observed on the teeth contacted with the composition.

The ammonium betaine employed in this example is prepared by adding about 131.55 parts by weight of distilled water, about 3.51 parts by weight of NaOH pellets, about 9.54 parts by weight of 2-chloropropionic acid, and about 30 parts by weight of dimethylaminopropyl palmitamide (Tegamine P-13 from Inolex Division of Wilson Pharmaceutical) to a reaction vessel with mixing. The reaction mass is mixed at about 90° C for about 8 hours to provide the amonium betaine.

EXAMPLE 21

Example 20 is repeated except that 0.1 ml of a composition of 1% by weight of N-carboxyethyl-N,N-dimethyl-N-(3-palmitamidopropyl) ammonium betaine and the remainder being distilled water is employed in place of the 0.1 ml composition used in Example 20. The results after the second 24-hour incubation period show that the composition provides complete inhibition of plaque and pellicle formation on the teeth and show very slight plaque and/or pellicle on the plastic strip.

The ammonium betaine employed in this example is prepared by adding about 131.55 parts by weight of distilled water, about 3.51 parts by weight of NaOH pellets, about 9.54 parts by weight of 3-chloropropionic acid, and about 30 parts by weight of Tegamine P-13 to a reaction vessel with mixing. Periodically hot distilled water is added to the reaction to maintain a solution. The reaction mass is mixed at about 90° C for about 8 hours to provide the ammonium betaine.

EXAMPLE 22

Example 20 is repeated except that 0.1 ml of a composition of 1% by weight of DL-N-carboxymethylmethyl-N,N-dimethyl-N-(3-oleylamidopropyl) ammonium betaine and the remainder being distilled water is employed in place of the 0.1 ml composition used in Example 20. The results after the second 24-hour incubation period show that the composition inhibits plaque and pellicle formation on the teeth.

The ammonium betaine used in this example is prepared by adding with stirring about 32.3 parts by weight of dimethylaminopropyloleamide (Tegamine O-13 from Inolex Division of Wilson Pharmaceutical) and about 9.5 parts by weight of 2-chloropropionic acid to a solution of about 3.5 parts by weight of sodium hydroxide in about 132 parts by volume of distilled water in a reaction vessel. The reaction mixture is mixed at about 80° C for about 8 hours during which time an additional 50 parts by volume of water are added. The reaction mass is then placed in a vacuum oven and heated to about 70° C for several hours to evaporate off the water. The remaining material is then dissolved in about 250 parts by volume of 95% ethanol and the insoluble NaCl is removed by filtration. The ethanol is then removed by evaporation and about 250 parts by volume of acetone are then added. Additional insoluble NaCl is removed by filtration.

The filtrate is then placed in a freezer whereby the desired compound separates out. Additional 400 parts by volume of acetone is added and after placing in a freezer the desired compound separates out. The product is then recrystallized using ethyl acetate and about 39.9 parts by weight of the product is obtained. An infrared scan of the product indicates that it is the desired ammonium betaine.

EXAMPLE 23

Example 20 is repeated except that 0.1 ml of a composition of 1% by weight of N-carboxyethyl-N,N-dimethyl-N-(3-oleylamidopropyl) ammonium betaine and the remainder being distilled water is employed in place of the 0.1 ml composition used in Example 20. The results after the second 24-hour incubation period show that the composition inhibits plaque and pellicle formation on the teeth.

The ammonium betaine used in this example is prepared by adding with stirring about 32.3 parts by weight of Tegamine 0-13 and about 9.5 parts by weight of 3-chloropropionic acid to a solution of about 3.5 parts by weight of sodium hydroxide in about 132 parts by volume of distilled water in a reaction vessel. The reaction mixture is mixed at about 80° C for about 7¼ hours. The reaction mass is then placed in a vacuum oven and heated to about 70° C for several hours to evaporate off the water. The remaining material is then dissolved in about 250 parts by volume of 95% ethanol and the insoluble NaCl is removed by filtration. About 100 parts by volume ethanol is then removed by evaporation, followed by cooling after which additional NaCl is removed by filtration. The remaining ethanol is evaporated off.

About 250 parts by volume of acetone are added and the composition is then placed in a freezer whereby the desired compound separates out. The proeuct is then recrystallized using ethyl acetate and about 35.4 parts by weight of the product is obtained. An infrared scan of the product indicates that it is the desired ammonium betaine.

EXAMPLE 24

Example 20 is repeated except that 0.1 ml of a composition of 1% by weight of DL-N-carboxymethylmethyl-N,N-dimethyl-N-(3-stearamidopropyl) ammonium betaine and the remainder being distilled water is employed in place of the 0.1 ml composition used in Example 20. The results after the second 24-hour incubation period show that the composition exhibits slight activity against plaque and pellicle formation on the teeth.

The ammonium betaine used in this example is prepared by adding with stirring about 16.25 parts by weight of dimethylaminopropyl stearamide (Tegamine S-13 from Inolex Division of Wilson Pharmaceutical) and about 4.8 parts by weight of 2-chloropropionic acid to a solution of about 1.78 parts by weight of sodium hydroxide in about 66 parts by volume of distilled water in a reacti vessel. The reaction mixture is mixed at about 80° C for about 7¼ hours after which time an additional 100 parts by volume of water are added. The reaction mass is then mixed for an additional 7 hours at this temperature. After this the reaction mass is then placed in a vacuum oven and heated to about 70° C for several hours to evaporate off the water. The remaining material is then dissolved in about 140 parts by volume of 95% ethanol and the insoluble NaCl is removed by filtration. The ethanol is then removed by evaporation and about 140 parts by volume of acetone are then added.

The material is then placed in a freezer after which it is filtered. The filtrate is then treated to evaporate acetone. The product is then recrystallized using ethyl acetate. An infrared scan of the product indicates that it is the desired ammonium betaine.

EXAMPLE 25

Example 20 is repeated except that 0.1 ml of a composition of 1% by weight of N-carboxyethyl-N,N-dimethyl-N-(3-stearamidopropyl) ammonium betaine and the remainder being distilled water is employed in place of the 0.1 ml composition used in Example 20. The results after the second 24-hour incubtion period show that the composition inhibits plaque and pellicle formation on the teeth.

The ammonium betaine used in this example is prepared by adding with stirring about 16.25 parts by weight of Tegamine S-13 and about 4.8 parts by weight of 3-chloropropionic acid to a solution of about 1.78 parts by weight of sodium hydroxide in about 66 parts by volume of distilled water in a reaction vessel. The reaction mixture is mixed at about 80° C for about 7½ hours during which time an additional 40 parts by volume of water are added. The reaction mass is then placed in a vacuum oven and heated to about 70° C for several hours to evaporate off the water. The remaining material is then dissolved in about 140 parts by volume of 95% ethanol and the insoluble NaCl is removed by filtration. The ethanol is then removed by evaporation and about 130 parts by volume of acetone are then added.

The composition is then placed in a freezer, after which the composition is filtered to yield about 18.3 parts by weight of the desired compound. An infrared scan of the product indicates that it is the desired ammonium betaine.

EXAMPLE 26

Example 20 is repeated except that 0.1 ml of a composition of 1% by weight of 2-[N,N-dimethyl-N-(3-palmitamidopropyl)-amino] ethanesulfobetaine and the remainder being propylene glycol is employed in place of the 0.1 ml composition used in Example 20. The results after the second 24-hour incubation period show that the composition exhibits activity against plaque and pellicle formation on the teeth. Only slight plaque growth is observed on the teeth and plastic.

The sulfobetaine used in this example is prepared by adding with stirring about 17 parts by weight of Tegamine P-13 to a solution of about 9.2 parts by weight of 2-chloroethanesulfonic acid, sodium salt monohydrate in about 80 parts by volume of distilled water in a reaction vessel. The reaction mixture is mixed at about 80° C for about 5 hours. An additional 25 parts by volume of distilled water are added and the reaction mass is heated for another 9 hours after which additional amounts of distilled water are added in incremental amounts of about 100 parts by volume, about 140 parts by volume, about 100 parts by volume, about 120 parts by volume, and about 140 parts by volume over a period of about 40 hours of heating at about 80° C. The reaction is maintained at about 80° C for another 16 hours. After this, the reaction mixture is dried in a vacuum oven under reduced pressure. The material recovered from the oven is then added to about 250 ml of 95% ethanol and the product is then obtained by filtration. An infrared scan of the product indicates that it is the desired sulfobetaine.

EXAMPLE 27

Example 20 is repeated except that 0.1 ml of a composition of 1% by weight of 2-[N,N-dimethyl-N-(3-oleylamidopropyl)-amino] ethanesulfobetaine and the remainder being propylene glycol is employed in place of the 0.1 ml composition used in Example 20. The results after the second 24-hour incubation period show that the composition exhibits activity against plaque and pellicle formation on the teeth. Very slight plaque growth is observed on teeth and plastic.

The sulfobetaine used in this example is prepared by adding with stirring about 18.3 parts by weight of Tegamine O-13 to a solution of about 9.2 parts by weight of 2-chloroethanesulfonic acid, sodium salt monohydrate in about 80 parts by volume of distilled water in a reaction vessel. The reaction mass is mixed at about 80° C for about 70 hours. After this, the reaction mass is placed in a vacuum oven at about 70° C under reduced pressure. The resulting solid material is then dissolved in about 150 parts by volume of 95% ethanol and the mixture is filtered after heating slightly. About 1.9 parts by weight of NaCl is collected. The filtrate is then evaporated. About 300 parts by volume of acetone are then added to the residue. Solid material separated out and then acetone is decanted off. The solid material is then placed in a desiccator after which remaining acetone evaporates. The solid product is then added to about 150 parts by volume of ethyl acetate and heated. The mixture is then cooled in a refrigerator, followed by filtration and then washing with ether to provide the desired product. An infra-red scan of the product indicates that it is the desired sulfobetaine.

What is claimed is:

1. A method for retarding pellicle and plaque formation on teeth which comprises intermittently contacting sites of plaque formation and growth with a preparation comprising an amount sufficient to retard said pellicle and plaque formation of a compound of the formula:

$$\left[ R \underset{}{\overset{O}{\overset{\|}{-}}} C - \underset{R_1}{\overset{}{N}} - A - \underset{R_2}{\overset{R_2}{\overset{|}{N^{\oplus}}}} - B - X^{\ominus} \right]_n$$

wherein R is a monovalent or divalent hydrocarbyl group containing at least 14 carbon atoms, $n$ is one when R is monovalent and is 2 when R is divalent; $R_1$ is H or a alkyl group containing from 1 to about 3 carbon atoms; A is a divalent hydrocarbon bridge containing from 1 to about 6 carbon atoms; each $R_2$ individually is an alkyl group containing from 1 to about 5 carbon atoms; or both $R_2$ groups are interconnected to form a heterocyclic ring with the N atom to which they are attached and contains 5 to 6 members in the ring, and being selected from the group consisting of morpholinyl, piperidinyl, pyrrolidinyl, and piperazinyl; B is a divalent alkylene or alkylidene group containing 1 or 2 carbon atoms, and X is a carboxylate or sulfonate group; and further provided that B contains 2 carbon atoms when X is a carboxylate group; or nontoxic, physiologically and orally acceptable salts of said compound; or mixtures thereof.

2. The method of claim 1 wherein R is a monovalent hydrocarbyl group.

3. The method of claim 1 wherein R is an aliphatic hydrocarbon group containing from 14 to about 21 carbon atoms.

4. The method of claim 1 wherein R is a monovalent aliphatic hydrocarbon group containing from 15 to about 17 carbon atoms.

5. The method of claim 1 wherein $R_1$ is hydrogen or methyl.

6. The method of claim 1 wherein $R_1$ is H.

7. The method of claim 1 wherein A is an alkylene or alkylidene group.

8. The method of claim 1 wherein A is an alkylene or alkylidene group containing 1 to 3 carbon atoms.

9. The method of claim 1 wherein each $R_2$ individually is an alkyl group containing from 1 to about 5 carbon atoms.

10. The method of claim 1 wherein $R_2$ is methyl.

11. The method of claim 1 wherein R is a monovalent hydrocarbyl group containing at least 14 carbon atoms; $R_1$ is H, A is an alkylene or alkylidene group containing from 1 to 3 carbon atoms and each $R_2$ group individually is methyl.

12. The method of claim 11 wherein R is an aliphatic hydrocarbon containing from 14 to about 21 carbon atoms.

13. The method of claim 11 wherein R is an aliphatic hydrocarbon containing from 15 to about 17 carbon atoms.

14. The method of claim 1 wherein B is $CH_2$.

15. The method of claim 1 wherein B contains 2 carbon atoms.

16. The method of claim 1 wherein X is $$\underset{O}{\overset{C-O.}{\overset{\|}{}}}$$

17. The method of claim 1 wherein said compound is DL-N-carboxymethylmethyl-N,N-dimethyl-N-(3-palmitamidopropyl) ammonium betaine; or nontoxic physiologically and orally acceptable salt thereof; or mixtures thereof.

18. The method of claim 1 wherein said compound is N-carboxyethyl-N,N-dimethyl-N-(3-palmitamidopropyl) ammonium betaine; or nontoxic physiologically and orally acceptable salt thereof; or mixtures thereof.

19. The method of claim 1 wherein said compound is DL-N-carboxymethylmethyl-N,N-dimethyl-N-(3-oleylamidopropyl) ammonium betaine; or nontoxic physiologically and orally acceptable salt thereof; or mixtures thereof.

20. The method of claim 1 wherein said compound is N-carboxyethyl-N,N-dimethyl-N-(3-oleylamidopropyl) ammonium betaine; or nontoxic physiologically and orally acceptable salt thereof; or mixtures thereof.

21. The method of claim 1 wherein said compound is DL-N-carboxymethylmethyl-N,N-dimethyl-N-(3-stearamidopropyl) ammonium betaine; or nontoxic physiologically and orally acceptable salt thereof; or mixtures thereof.

22. The method of claim 1 wherein said compound is N-carboxyethyl-N,N-dimethyl-N-(3-stearamidopropyl) ammonium betaine; or nontoxic physiologically and orally acceptable salt thereof; or mixtures thereof.

23. The method of claim 1 wherein said compound is 2-[N,N-dimethyl-N-(3-palmitamidopropyl)-amino] ethanesulfobetaine; or nontoxic physiologically and orally acceptable salt thereof; or mixtures thereof.

24. The method of claim 1 wherein said compound is 2-[N,N-dimethyl-N-(3-oleylamidopropyl)-amino] ethanesulfobetaine; or nontoxic physiologically and orally acceptable salt thereof; or mixtures thereof.

25. The method of claim 1 wherein said compound is 2-[N,N-dimethyl-N-(3-stearamidopropyl)-amino] ethanesulfobetaine; or nontoxic physiologically and orally acceptable salt thereof; or mixtures thereof.

26. The method of claim 1 which comprises intermittently contacting the oral cavity.

27. The method of claim 1 wherein said preparation contains at least about 1% by weight of the compound.

28. The method of claim 1 wherein the preparation has a pH between about 5 and about 7.5.

29. The method of claim 1 wherein said preparation also contains from about 5 to about 60% by weight of a abrasive polishing agent; from about 0.5% to about 5% by weight of a sudsing agent; from about 0.1 to about 15% by weight of a thickening agent; water and humectants.

30. The method of claim 1 wherein said preparation is in the form of a prophylactic paste which further includes pumice.

31. The method of claim 1 wherein said preparation contains water and ethyl alcohol.

32. The method of claim 1 wherein said preparation further contains silica gel, sorbitol, and water.

33. The method of claim 1 wherein said preparation further includes glycerin, hydroxyethyl cellulose, propylene glycol, and water.

34. A dental preparation for retarding pellicle and plaque formation on teeth which comprises an amount sufficient to retard said pellicle and plaque formation of a compound of the formula:

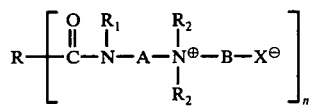

wherein R is a monovalent or divalent hydrocarbyl group containing at least 14 carbon atoms, $n$ is one when R is monovalent and is 2 when R is divalent; $R_1$ is H or an alkyl group containing from 1 to about 3 carbon atoms; A is a divalent hydrocarbon bridge containing from 1 to about 6 carbon atoms; each $R_2$ individually is an alkyl group containing from 1 to about 5 carbon atoms; or both $R_2$ groups are interconnected to form a heterocyclic ring with the N atom to which they are attached and contains 5 to 6 members in the ring, and being selected from the group consisting of morpholinyl, piperidinyl, and piperazinyl; B is a divalent alkylene or alkylidene group containing 1 or 2 carbon atoms; and X is a carboxylate or sulfonate group; and further provided that B contains 2 carbon atoms when X is a carboxylate group; or nontoxic, physiologically and orally acceptable salts of said compound; or mixtures thereof; from about 5 to about 60% by weight of an abrasive polishing agent; from about 0.5 to about 5% by weight of a sudsing agent; from about 0.1 to about 15% by weight of a thickening agent; water and humectants.

35. A dental preparation in the form of a prophylactic paste for retarding pellicle and plaque formation on teeth which comprises an amount sufficient to retard said pellicle and plaque formation of a compound of the formula:

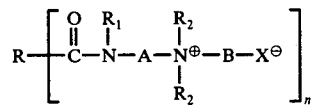

wherein R is a monovalent or divalent hydrocarbyl group containing at least 14 carbon atoms; $n$ is one when R is monovalent and is 2 when R is divalent; $R_1$ is H or an alkyl group containing from 1 to about 3 carbon atoms; A is a divalent hydrocarbon bridge containing from 1 to about 6 carbon atoms; each $R_2$ individually in an alkyl group containing from 1 to about 5 carbon atoms; or both $R_2$ groups are interconnected to form a heterocyclic ring with the N atom to which they are attached and contain 5 to 6 members in the ring, and being selected from the group consisting of morpholinyl, piperidinyl, pyrrolidinyl, and piperazinyl; B is a divalent alkylene or alkylidene group containing 1 or 2 carbon atoms, and X is a carboxylate or sulfonate group; and further provided that B contains 2 carbon atoms when X is a carboxylate group; or nontoxic; physiologically and orally acceptable salts of said compound; or mixtures thereof; and pumice.

36. The method of claim 1 wherein said preparation further includes hydrated alumina.

37. The method of claim 1 wherein said preparation further includes a polyoxyalkylene polyol.

38. The method of claim 1 wherein X is a sulfonate group.

39. The method of claim 1 wherein R is an aliphatic hydrocarbon group.

40. The method of claim 1 wherein each $R_2$ individually is an alkyl group containing from 1 to 3 carbon atoms.

41. The method of claim 1 wherein the preparation contains from about 5 to about 25% by weight of the compound.

42. The method of claim 1 wherein said preparation is in the form of a mouthwash and further includes a sudsing agent; ethyl alcohol; a humectant; sweetener; flavoring agent; and water.

43. The method of claim 1 wherein said preparation further includes sorbitol, silica, propylene glycol and water.

44. The method of claim 1 wherein said preparation further includes sorbitol, glycerin, carboxymethyl cellulose, silica gel, water, and hydrated alumina.

45. The method of claim 1 wherein said preparation further includes polyoxypropyleneoxyethylene, carboxymethyl cellulose, sorbitol, hydrated alumina, silica gel, glycerin, and water.

46. A dental preparation in the form of a mouthwash for retarding pellicle and plaque formation on teeth which comprises an amount sufficient to retard said pellicle and plaque formation of a compound of the formula:

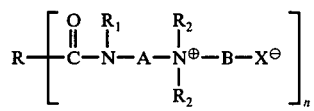

wherein R is a monovalent or divalent hydrocarbyl group containing at least 14 carbon atoms; $n$ is one when R is monovalent and is 2 when R is divalent; $R_2$ is H or an alkyl group containing from 1 to about 3 carbon atoms; A is a divalent hydrocarbon bridge containing from 1 to about 6 carbon atoms; each $R_2$ individually is an alkyl group containing from 1 to about 5 carbon atoms; or both $R_2$ groups are interconnected to form a heterocyclic ring with the N atom to which they are attached and contains 5 to 6 members in the ring, and being selected from the group consisting of morpholinyl, piperidinyl, pyrrolidinyl, and piperazinyl; B is a divalent alkylene or alkylidene group containing 1 or 2 carbon atoms, and X is a carboxylate or sulfonate group; and further provided that B is 2 carbon atoms when X is a carboxylate group; or nontoxic, physiologically and orally acceptable salts of said compound; or mixtures thereof; a sudsing agent, ethyl alcohol, a humectant, sweetener, flavoring agent, and water.

* * * * *